(12) United States Patent
Schmedtje, Jr.

(10) Patent No.: US 10,501,471 B1
(45) Date of Patent: Dec. 10, 2019

(54) COMPOUNDS USEFUL FOR TREATING CARDIOVASCULAR DISEASES

(71) Applicant: John Frederick Schmedtje, Jr., Roanoke, VA (US)

(72) Inventor: John Frederick Schmedtje, Jr., Roanoke, VA (US)

(73) Assignee: John F. Schmedtje, Jr., Roanoke, VA (US)

( * ) Notice: Subject to any disclaimer, the term of this patent is extended or adjusted under 35 U.S.C. 154(b) by 0 days.

(21) Appl. No.: 16/429,015

(22) Filed: Jun. 2, 2019

Related U.S. Application Data

(60) Provisional application No. 62/755,516, filed on Nov. 4, 2018.

(51) Int. Cl.
*C07D 493/04* (2006.01)
*A61K 31/343* (2006.01)

(52) U.S. Cl.
CPC .......... *C07D 493/04* (2013.01); *A61K 31/343* (2013.01)

(58) Field of Classification Search
CPC ........................... C07D 493/04; A61K 31/343
See application file for complete search history.

(56) References Cited

U.S. PATENT DOCUMENTS

| | | | | |
|---|---|---|---|---|
| 4,363,805 A | * | 12/1982 | Klessing | C07D 493/04 514/166 |
| 4,769,379 A | * | 9/1988 | Leitold | C07D 493/04 514/290 |
| 8,211,939 B2 | * | 7/2012 | Del Castillo Nieto | C07D 493/04 514/470 |

* cited by examiner

*Primary Examiner* — D Margaret M Seaman

(57) ABSTRACT

The present invention provides novel compounds and pharmaceutical compositions thereof and methods of using the same for treating cardiovascular diseases.

20 Claims, No Drawings

COMPOUNDS USEFUL FOR TREATING CARDIOVASCULAR DISEASES

CROSS-REFERENCE TO RELATED APPLICATIONS

This application claims the benefit of U.S. Provisional Patent Application No. 62/755,516, filed Nov. 4, 2018, which is incorporated by reference herein in its entirety.

FIELD OF THE INVENTION

The present invention provides novel compounds and pharmaceutical compositions thereof and methods of using the same for treating cardiovascular diseases.

BACKGROUND OF THE INVENTION

According to 2019 American Heart Association Heart Disease and Stroke statistics (Benjamin, et al., 2019) cardiovascular diseases are responsible for most of the deaths in the United States. These diseases are found in 121,000,000 US citizens over the age of 20, or 48% of the adult population. All of these cardiovascular diseases are linked to cellular hypoxia. Cellular hypoxia is defined as a relative deficiency in the availability or utilization of oxygen in a living cell compared to normal physiological conditions.

The annual costs of cardiovascular diseases in the United States will reach $1.1 trillion in 2035. Despite tremendous progress in the management of cardiovascular diseases these same diseases remain the most frequent causes of death in the US, and must be considered a worldwide problem as well. In 2016, about 17.6 million deaths were attributed to cardiovascular diseases globally, an increase of 14.5% from 2006.

Health professionals point with some pride to the substantial decreases in the death rate due to cardiovascular diseases in the US in recent years. However, the patients who once died of these diseases acutely have now become chronic patients in need of long term management. The challenge to us as a society is to devise low cost management strategies that will address this growing epidemic.

When oxygen is in short supply, cellular metabolism and therefore life itself is jeopardized. Living cells respond to a change in the amount of ambient oxygen available with an exquisitely sensitive mechanism that reprograms pathways of gene expression. The nature of the response is particular to the context and environment of each cell. Hypoxia inducible factors (HIFs) are found in organisms ranging from primitive worms to humans, wherever delivery of oxygen is an important variable in the life of an organism, and there are many current pharmaceutical development programs devoted to alteration of HIF physiology. (Semenza, 2019) HIFs provide us with an important illustration of a key component of hypoxia-mediated gene expression, but the range of human cellular responses to oxygen is not limited to modulation of HIF expression.

Hypoxia is a correlate of hypoperfusion, and hypoxia is noted in cardiovascular diseases, as well as other conditions associated with decreased blood flow to a perfused organ. Reperfusion is associated with the return of blood flow. Reperfusion is ordinarily desirable, but prolonged ischemia and subsequent return of blood flow can lead to local inflammation and cell injury due to toxic byproducts of oxidative metabolism. There is a way to mitigate this process. Repetitive brief hypoperfusion and reperfusion can increase the tolerance to future ischemic events. This phenomenon is known as preconditioning. An effective treatment for the adverse consequences of nonlethal severe decreases in oxygen delivery and perfusion has been highly sought after and the therapeutic options are limited at this time.

Most compounds presently under clinical development for management of hypoxia-related gene expression inhibit the prolyl hydroxylases. Prolyl hydroxylases cause hypoxia inducible factor to breakdown. If you inhibit prolyl hyrdoxylases, then you inhibit the agent that causes breakdown of HIF, and the double negative in effect potentiates HIF. Prolyl hydroxylase inhibitors are compounds that potentiate the adaptive response of cells to hypoxia on a systemic basis via the HIFs. HIF, potentiated by prolyl hydroxylase inhibitors, can cause the kidney to synthesize extra erythropoietin, an endogenous molecule that stimulates red blood cell development to therapeutic effect in the setting of anemia. HIF potentiation also leads to angiogenesis, leading to greater blood vessel growth to hypoxic regions, which can be beneficial when, for example, coronary artery disease leads to myocardial ischemia and associated cardiac dysfunction. Unfortunately, the same global approach may simultaneously increase the arterial supply of dormant malignancies, and/or alter cell metabolism to conserve oxygen where oxygen is already available. It is easy to underestimate the complexity of the pathophysiology of hypoxia-related disease states. A very selective approach to regulation of hypoxia-mediated events will be required to develop safe and effective pharmaceuticals. This will involve delivery within a limited organ-specific space or triggering of activity in the proper pathological context.

The expression of cyclooxygenase-2 (COX-2) is transcriptionally regulated by hypoxia in human umbilical vein endothelial cells in culture via the transactivation factors NF-κB p65, HMG I(Y), and Sp1, leading to increased production of $PGE_2$. (Schmedtje et al., 1997; Xu et al., 2000; Ji et al., 1998) These discoveries reflect the fact that HIFs are insufficient to drive all of the human adaptations to hypoxia, and that NF-κB is another important mediator of hypoxia-driven transactivation of genes in the vascular endothelium.

Ischemic cardiovascular diseases are associated with a lack of blood flow and are also associated with hypoxia. Ischemic preconditioning is a portion of the therapeutic effect attributed to the present compounds. Vascular endothelial expression of COX-2 is increased by hypoxia. COX-2 is essential for ischemic preconditioning as a companion to the synthesis of nitric oxide (NO). (Li, Q. et al., 2007) Both are required in order to achieve the protection of the heart that is conferred by the late phase of ischemic preconditioning. (Guo et al., 2012)

The SLC14 (solute carrier 14) family of urea transporter genes regulate urea transport across cell membranes. UT-B (urea transport protein, B, the product of the gene SLC14A1) facilitates transport of urea, water and urea analogues across cell membranes. (Shayakul et al., 2013) UT-B is expressed widely, including in the heart, vascular endothelium and erythrocytes. UT-B null mice have cardiac conduction abnormalities, increased brain urea concentration and decreased NO production. (Li, X. et al., 2012) Urea is freely permeable and enters cells passively, but the equilibrium is slow, and UT-B facilitates the rapid expulsion of urea from erythrocytes. (Sands, 1999) Urea is generally considered a waste product and it carries nitrogen from the breakdown of amino acids to recycling opportunities. Renal failure is associated with decreased nitric oxide synthase (NOS) activity. However, rats with normal renal function do not have decreased NOS activity when BUN is raised to uremic levels. (Xiao et al., 2001) Urea may have cardioprotective properties in some contexts (Wang et al., 1999)

Membrane UT-B is abundant on human vascular endothelium in culture derived from various locations and appears to participate in regulation of nitric oxide (NO) synthesis. (Wagner et al., 2002) Pharmacological inhibition of UT-B in the vascular endothelium causes intracellular accumulation of urea. This is believed to lead to a feedback inhibition on arginase (the enzyme that converts 1-arginine to urea) that elevates the activity and expression of the alternative pathway for 1-arginine, in this case endothelial NOS, (eNOS) enabling increased production of NO. (Sun et al., 2016)

Hypoxia increases the expression of UT-B in hypoxic vascular endothelium. The inventor found that messenger RNA for the gene for UT-B (SLC14A1) is significantly upregulated in human vascular endothelial cells in hypoxic (1% oxygen) cell culture. The upregulation of expression of UT-B in this setting will pump urea out of the endothelial cell and remove the feedback inhibition of arginase that causes increased eNOS activity, reducing the net vasodilator effect of nitrate administration. A source of urea or a urea analogue should maintain effective intracellular urea substrate levels and route 1-arginine to eNOS production of NO, augmenting vasodilatation in response to hypoxia, dilating adjacent vascular smooth muscle.

It would be beneficial to discover compounds that potentiate vasodilatory release of NO in hypoxia while enabling the process of ischemic preconditioning in a targeted (e.g., local) manner, thus leading to the treatment and prevention of major adverse cardiac events in cardiovascular diseases.

SUMMARY OF THE INVENTION

Accordingly, in an aspect, the present invention provides novel compounds or pharmaceutically acceptable salts thereof that respond to areas of cellular hypoxia.

In another aspect, the present invention provides novel pharmaceutical compositions, comprising: a pharmaceutically acceptable carrier and a therapeutically effective amount of at least one of the compounds of the present invention or a pharmaceutically acceptable salt thereof.

In another aspect, the present invention provides novel methods for treating diseases mediated by cellular hypoxia, comprising: administering to a mammal in need thereof a therapeutically effective amount of at least one of the compounds of the present invention or a pharmaceutically accetable salt thereof.

In another aspect, the present invention provides processes for preparing at least one of the compounds of the present invention.

In another aspect, the present invention provides novel compounds or pharmaceutically acceptable salts for use in therapy.

In another aspect, the present invention provides the use of novel compounds for the manufacture of a medicament for the treatment of diseases mediated by cellular hypoxia.

These and other objects, which will become apparent during the following detailed description, have been achieved by the inventors' discovery that the presently claimed compounds or pharmaceutically accetable salts thereof are expected to provide a therapeutic response focused in areas of cellular hypoxia.

DETAILED DESCRIPTION OF THE INVENTION

All references cited herein are hereby incorporated in their entirety herein by reference.

The present compounds are designed to release nitrate in addition to urea or a urea analogue (e.g., amide or glycolamide) at the endothelial surface. They are small molecules with a central isosorbide moiety attached to a urea moiety (Formula I), amide moiety (Formula II), or glycolamide moiety (Formula III)) and a nitrate group (—$NO_3$). Glycolamide has the benefit of relatively high permeability via UT-B and low toxicity. (Zhao et al., 2007.) The present compounds are expected to take advantage of the passive movement of urea and urea analogues across the cell membrane into the vascular endothelial cell. But there is increased expression of the UT-B gene in the setting of vascular endothelial hypoxia. UT-B-mediated transport (removal) of urea and urea analogues occurs in hypoxia, and this appears to limit eNOS activity. Replacement of the intracellular urea will therefore augment the effect of the nitrate provided to the vascular endothelium. It is expected that the combination of urea and/or urea analogues as well as nitrate in the setting of hypoxia will create a cascade of events including vasodilatation and ischemic preconditioning.

The present compounds feature a nitrate group that can be metabolized via aldehyde dehydrogenase-2 to NO, or can be transformed to nitrite and subsequently reduced by a range of enzymes including xanthine oxidase to form NO. Alternatively, intracellular L-arginine is oxidized by nitric oxide synthase to form NO. NO, historically known as the endothelium-derived relaxation factor, induces the formation of cyclic guanosine monophosphate (cGMP) via activation of soluble guanylate cyclase, the NO receptor. cGMP binds and enhances protein kinase G activity, promoting movement of calcium out of the smooth muscle cells, thereby reducing vascular tone since reduced intracellular calcium impairs smooth mucle contractility.

NO is also essential to ischemic preconditioning, although the exact intracellular mechanisms of this effect are not as well understood as those of vasodilation. COX-2 expression is a necessary part of ischemic preconditioning, and COX-2 expression is induced by hypoxia, via a mechanism that depends on the NF-κB transactivation system. Furthermore, endothelial nitric oxide synthase appears to be slightly downregulated when hypoxia causes upregulation of COX-2, as previously published. (Schmedtje et al., 1997) Therefore a mechanism of augmenting NO production with the induction of COX-2 in the setting of hypoxia will be of therapeutic value in the vascular endothelium.

Thus, in an aspect, the compounds of the present invention will potentiate formation and release of vasodilatory NO while enabling the process of ischemic preconditioning in a targeted manner.

In another aspect, the compounds of the present invention facilitate the UT-B transport of urea and/or analogues across the cell membrane by providing more substrate for transport.

In another aspect, since the present compounds are not global modulators of HIF (hypoxia inducible factor) effects, their therapeutic response will be focused in areas of cellular hypoxia. By locally alleviating cellular hypoxia, the present compounds can treat cardiovascular diseases with little or none of the side effects seen with global hypoxia therapies.

In another aspect, the present invention provides novel compounds of formula I, II, and/or III:

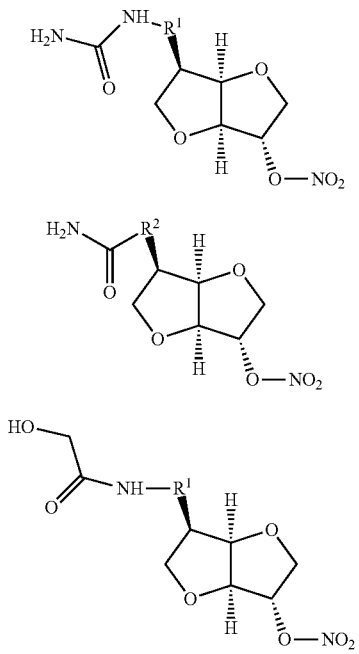

wherein:
R¹ is absent;
alternatively, R¹ is selected from (the right-hand portion of R² being attached to the isosorbide moiety): $(CH_2)_2O$, $(CH_2)_2NH$, $(CH_2)_3O$, $(CH_2)_3NH$, $CH_2C(=O)O$, and $CH_2C(=O)NH$; and,
R² is selected from (the right-hand portion of R² being attached to the isosorbide moiety): $(CH_2)_2O$, $(CH_2)_2NH$, $(CH_2)_3O$, $(CH_2)_3NH$, $CH_2C(=O)O$, $CH_2C(=O)NH$, $CH_2OC(=O)O$, $CH_2OC(=O)NH$, $CH_2NHC(=O)O$, and $CH_2NHC(=O)NH$;
or a pharmaceutically acceptable salt thereof.

In another aspect, the compound is of formula I or a pharmaceutically acceptable salt thereof.

In another aspect, the compound is of formula I and R¹ is absent or a pharmaceutically acceptable salt thereof.

In another aspect, the compound is of formula I and R¹ is selected from: $(CH_2)_2O$, $(CH_2)_2NH$, $(CH_2)_3O$, and $(CH_2)_3NH$ or a pharmaceutically acceptable salt thereof.

In another aspect, the compound is of formula II or a pharmaceutically acceptable salt thereof.

In another aspect, the compound is of formula II and R² is selected from: $(CH_2)_2O$, $(CH_2)_2NH$, $(CH_2)_3O$, $(CH_2)_3NH$, $CH_2OC(=O)O$, $CH_2OC(=O)NH$, $CH_2NHC(=O)O$, and $CH_2NHC(=O)NH$ or a pharmaceutically acceptable salt thereof.

In another aspect, the compound is of formula III or a pharmaceutically acceptable salt thereof.

In another aspect, the compound is of formula III and R¹ is absent or a pharmaceutically acceptable salt thereof.

In another aspect, the compound is of formula III and R¹ is selected from: $(CH_2)_2O$, $(CH_2)_2NH$, $(CH_2)_3O$, and $(CH_2)_3NH$ or a pharmaceutically acceptable salt thereof.

In another aspect, the present invention provides novel pharmaceutical compositions, comprising: a pharmaceutically acceptable carrier and a therapeutically effective amount of a compound of the present invention or a pharmaceutically accetable salt thereof.

In another aspect, the present invention provides a novel method of treating a disease mediated by cellular hypoxia, comprising: administering to a patient in need thereof a therapeutically effective amount of at least one compound of the present invention or a pharmaceutically accetable salt thereof.

In another aspect, the present invention provides a novel method for treating a cardiovascular disease, comprising: administering to a patient in need thereof a therapeutically effective amount of at least one compound of the present invention or a pharmaceutically accetable salt thereof.

In another aspect, the cardiovascular disease is selected from: coronary artery disease, myocardial infarction, heart failure, cardiac arrrhythmia, electrophysiological disorders of the heart, congenital cardiovascular anomalies, developmental cardiovascular anomalies, inflammatory cardiomyopathy, Kawasaki disease, infectious cardiomyopathy, sudden death/cardiac arrest, atherosclerosis, atherosclerotic cardiovascular diseases, cardiac valve disease, venous insufficiency, cardiac thrombosis, vascular thrombosis, thromboembolism, peripheral arterial disease, aortic aneurysm, aortic dissection, vascular aneurysm, vascular dissection, stroke, systemic hypertension, and pulmonary hypertension.

In another aspect, the present invention provides a compound of the present invention for use in therapy.

In another aspect, the present invention provides the use of the present invention for the manufacture of a medicament for the treatment of a disease mediated by cellular hypoxia.

In another aspect, the present invention provides the use of the present invention for the manufacture of a medicament for the treatment of a cardiovascular disease.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

Cellular hypoxia is a lack of oxygen at the level of individual cells, not necessarily related to a lack of oxygen at the level of a whole organism or an environment.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Mammal" and "patient" cover warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycolylarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the indication listed herein. "Therapeutically effective amount" also includes an amount of the combination of compounds claimed that is effective to treat the desired indication. The combination of compounds can be a synergistic combination. Synergy, as described, (Chou & Talalay, 1984) occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Compounds of the present invention are expected to be active as described herein.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal); subdermal implants; and, buccal, sublingual, topical, rectal, vaginal, and intranasal administrations. Examples of oral formulations include tablets, coated tablets, hard and soft gelatin capsules, solutions, emulsions, and suspensions. Bioerodible, non-bioerodible, biodegradable, and non-biodegradable systems of administration may also be used, including drug-eluting structures such as stents, placed by catheter, that may deliver the present compounds directly to a vessel wall.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the compound of the present invention administered daily will vary on an individual basis and to some extent may be determined by the severity of the disease being treated. The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Capsule |
|---|---|
| Active ingredient | 50 |
| Crystalline lactose | 60 |
| Microcrystalline cellulose | 39 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the magnesium stearate is admixed. The final mixture is filled into hard gelatin capsules of suitable size.

A possible example of an injection solution of the present invention is as follows.

| Ingredient | mg/Solution |
|---|---|
| Active substance | 1.0 mg |
| 1 N HCl | 20.0 μl |
| acetic acid | 0.5 mg |
| NaCl | 8.0 mg |
| Phenol | 10.0 mg |
| 1 N NaOH | q.s. ad pH 5 |
| H$_2$O | q.s. ad 1 mL |

Other features of the invention will become apparent in the course of the following descriptions of exemplary embodiments that are given for illustration of the invention and are not intended to be limiting thereof.

SYNTHESIS EXAMPLES

The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Synthesis Examples 1-17 are representative of the procedures that can be used to prepare compounds of the present invention. Known compounds isosorbide-5-mononitrate (2-hydroxy-1,4:3,6-dianhydro-L-glucitol 5-nitrate) and 2-amino-isosorbide-5-mononitrate (2-amino-1,4:3,6-dianhydro-L-glucitol 5-nitrate) are used as starting materials for the examples.

Synthesis Example 1

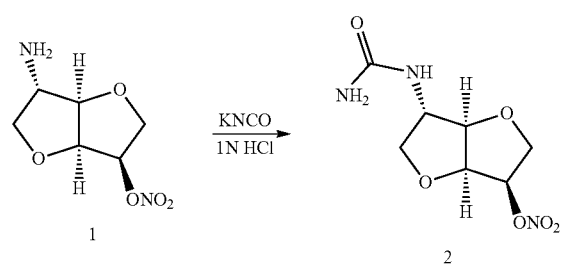

2-Amino-isosorbide-5-mononitrate (1) 1N HCl solution can be treated with potassium isocyanate at room temperature with stirring for 10-12 hours to afford the 2-ureido derivative (2) upon conventional work-up via extraction.

Synthesis Example 2

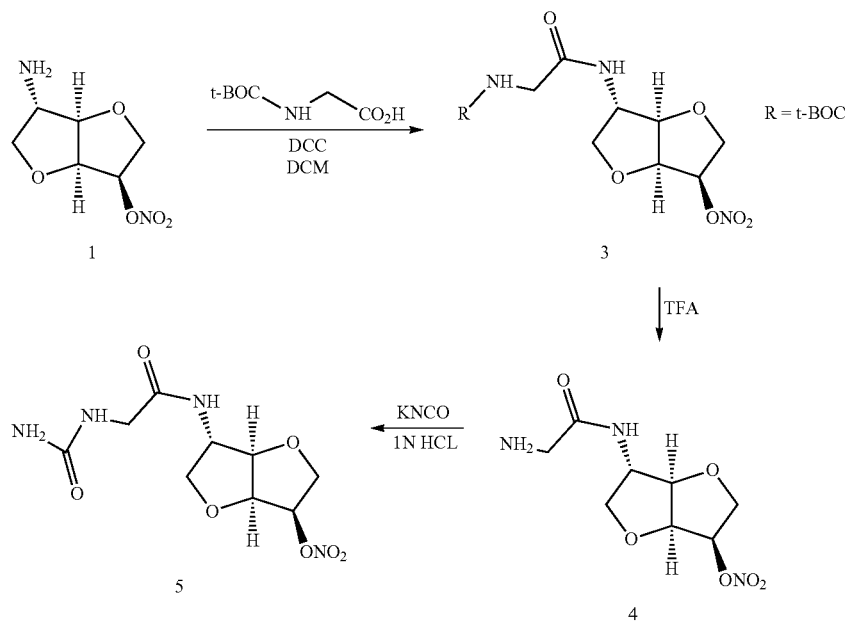

2-Amino-isosorbide-5-mononitrate (1) can be treated with N-t-BOC-glycine (t-BOC=tertiary butyl-oxycarbonyl) in dichloromethane in the presence of N,N'-dicyclohexyl-carbodiimide (DCC) and dimethyl-aminopyridine (DMAP). After overnight stirring at ambient temperature, the t-BOC amide (3) can be isolated in the conventional manner. Subsequent treatment of (3) with trifluoroacetic acid can provide the de-protected amino acid adduct (4) which upon treatment with potassium isocyanate and dilute HCl solution as previously described can afford the ureido glycine adduct (5).

Synthesis Example 3

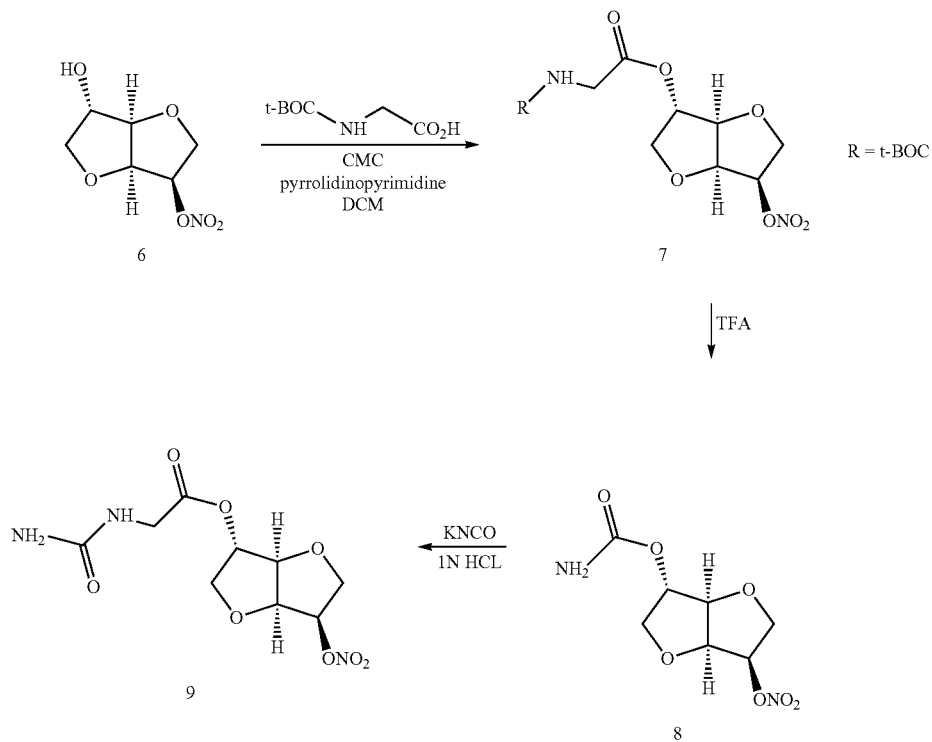

Treatment of isosorbide-5-mononitrate (6) in dichloromethane (DCM) with 1-cyclohexyl-3-(2-morpholinyl)carbodiimide (CMC) in the presence of pyrrolidinopyrimidine can afford the protected amino acid addict (7). Removal of the protecting group with TFA (trifluoro-acetic acetate) can provide the amino compound (8). Subsequent treatment with potassium isocyanate and dilute HCl solution at 0° C. to ambient temperature can yield the urea compound (9).

Synthesis Example 4

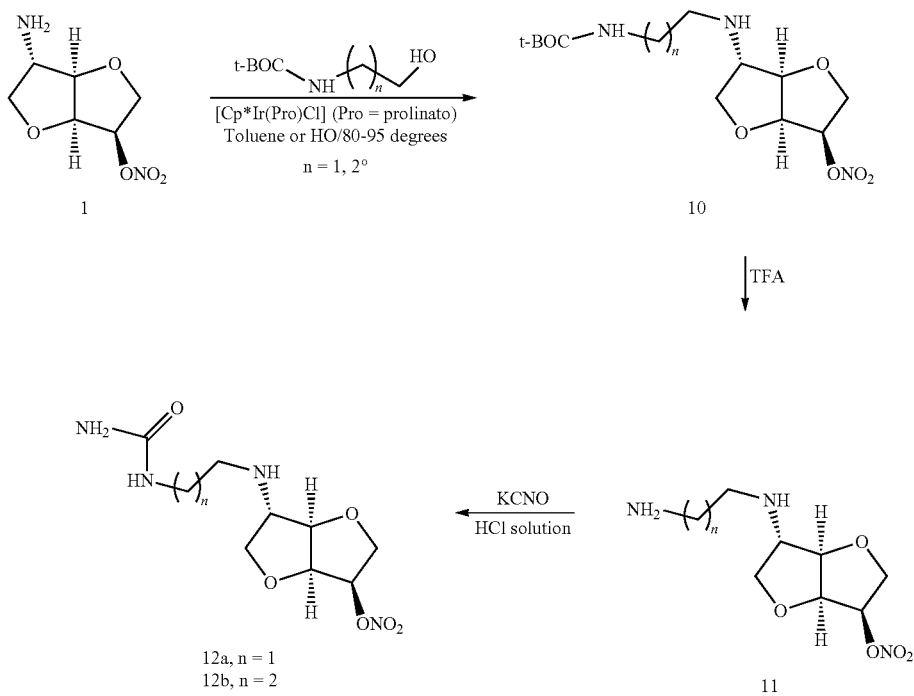

Treatment of 2-amino-isosorbide-5-mononitrate (1) with t-BOC-amino ethanol or t-BOC-3-aminopropanol in toluene or water in the presence of [Cp*Ir(Pro)Cl] (Pro=prolinato) (Cp=cyclopentadienyl) can afford the protected diamino adducts (10). Removal of the protecting group with TFA can afford the primary amines (11), which can be converted to the ureas (12a, 12b) using potassium cyanate in dilute hydrochloric acid solution, as previously described.

Synthesis Example 5

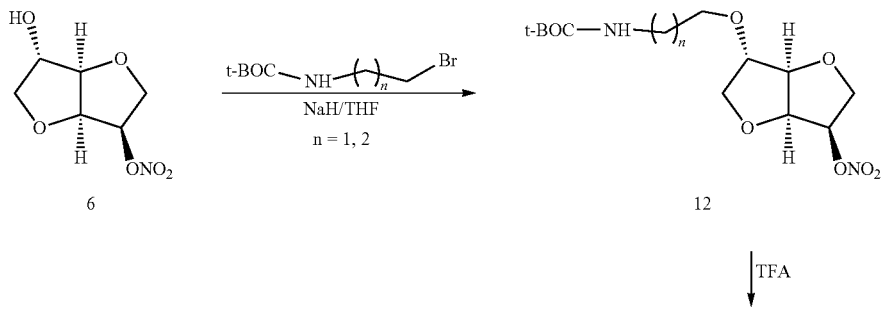

-continued

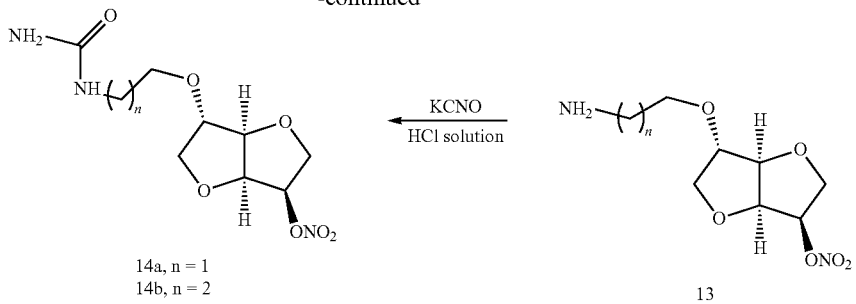

14a, n = 1
14b, n = 2

13

Isosorbide-5-mononitrate (6) can be deprotonated with sodium hydride or lithium di-isopropyl amide in tetrahydrofuran (THF) and then treated with with t-BOC-amino ethyl bromide or t-BOC-3-aminopropyl bromide to give the ethers (12). Deprotection of the t-BOC group using TFA will give the primary amine (13) and subsequent treatment potassium isocyanate as previously described can give the ureas (14).

Synthesis Example 6

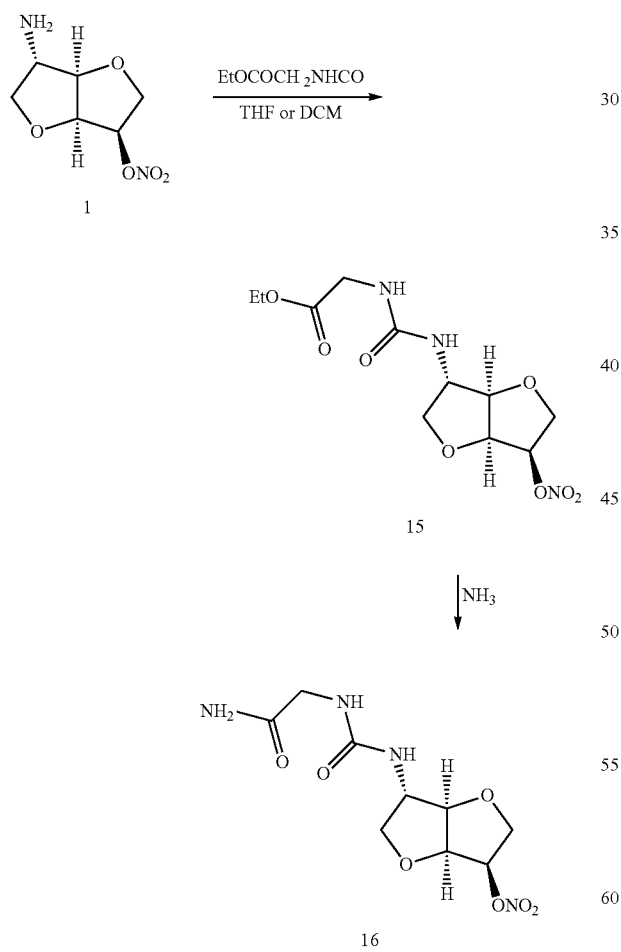

Treatment of 2-amino-isosorbide-5-mononitrate (1) with ethylcyananoacetate in THF or DCM can yield the urea (15). Further reaction with anhydrous ammonia in methanol can produce the ureido carboxamide (16).

Synthesis Example 7

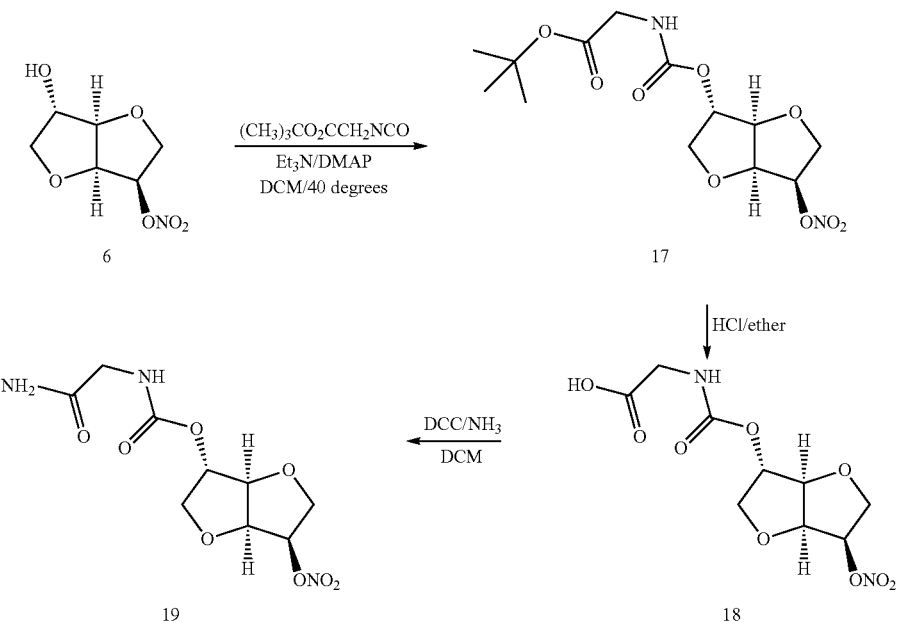

Treatment of isosorbide-5-mononitrate (6) with t-butyl-cyanoacetate in acetonitrile in the presence of N-methyl imidazole can yield the carbamate (17). Removal of the t-butyl group can be achieved with HCl in ether or with TFA to give the carboxylic acid (18). Amidation of the acid with ammonia in the presence of DCC can provide the carboxamide (19).

Synthesis Example 8

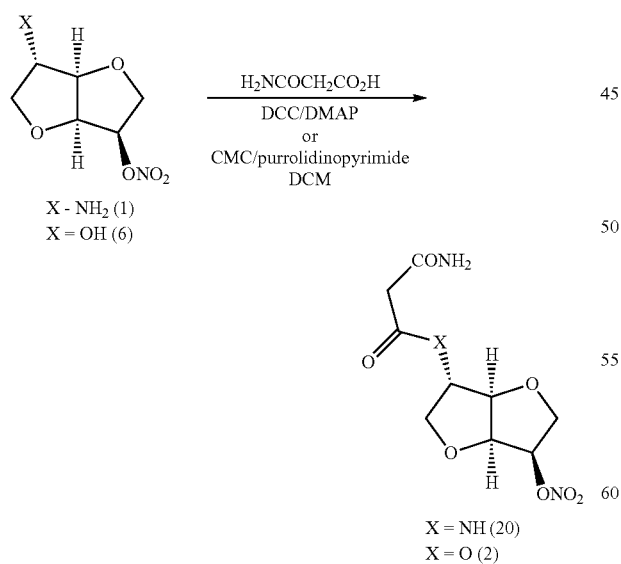

Treatment of 2-amino-isosorbide-5-mononitrate (1) or isosorbide-5-mononitrate (6) with malonic acid monoamide in DCM in the presence of DCC/DMAP or CMC/pyrrolidinopyrimidine can produce the malonamide (20) or the malono-ester-amido (21), respectively.

Synthesis Example 9

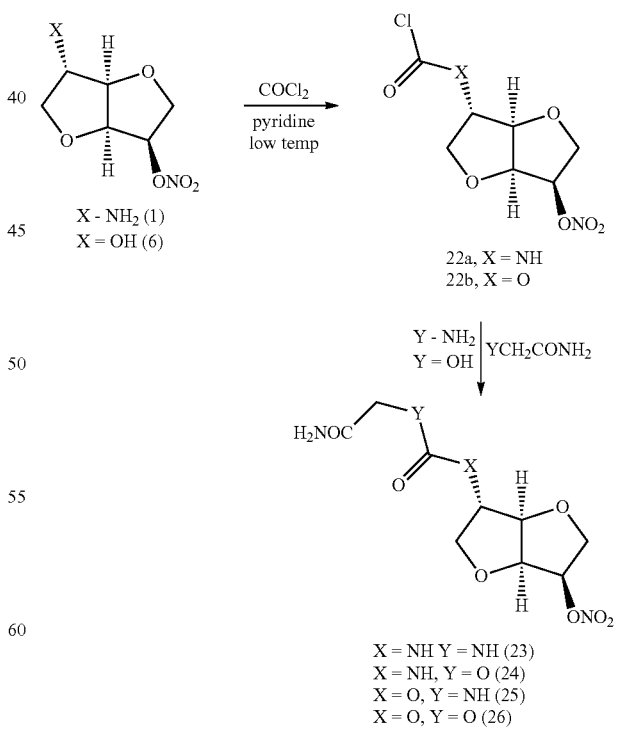

Treatment of 2-amino-isosorbide-5-mononitrate (1) with phosgene and pyridine at about 0° C. can produce the carbamoyl chloride (22a, X=NH). Reaction of this carbamoyl chloride with glycinamide at low temperatures in the presence of DMAP in DCM can afford the ureido carboxamide (23). Alternatively, the carbamoyl chloride (22) (X=NH) can be treated with glycolamide in the presence of DMAP in DCM and to afford the carbonate with the terminal carboxamide group (24). If 2-amino-isosorbide-5-mononitrate (6) is used as the starting material for this sequence, the phosgene reaction can produce the carbonyl chloride at low temperature (22, X=O) and if this intermediate is treated with glycinamide or glycolamide under the conditions previously described, the carbamate (25) or the carbonate (26), respectively, can be prepared.

Synthesis Example 10

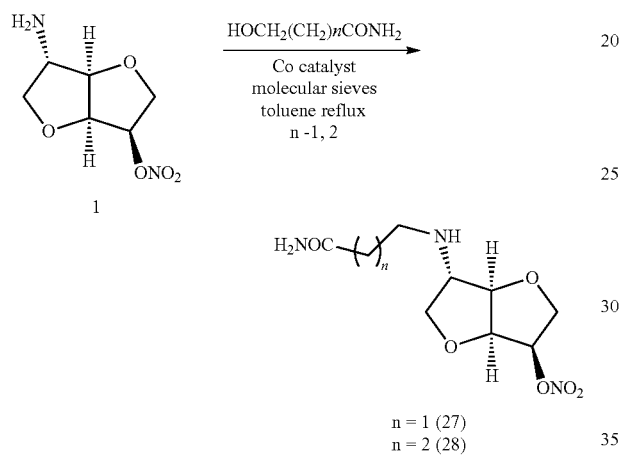

Treatment of 2-amino-isosorbide-5-mononitrate (1) with 3-hydroxypropionamide or 4-hydroxy butanamide in the presence of cobalt catalyst and molecular sieves in toluene at elevated temperatures can produce the carboxamido-amines (27) and (28), respectively.

Synthesis Example 11

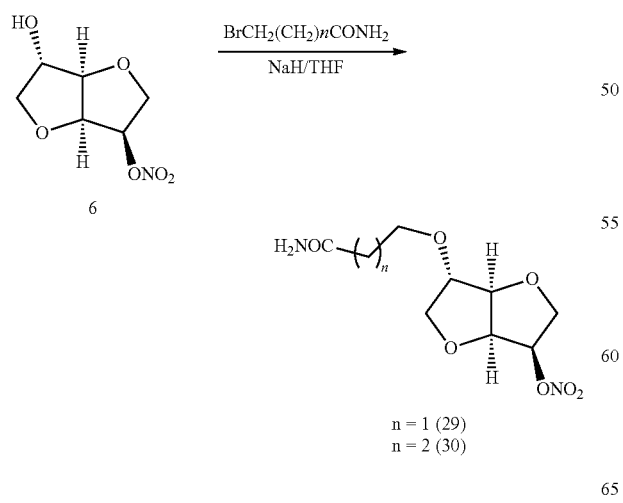

Treatment of isosorbide-5-mononitrate (6) with sodium hydride in THF or lithium diisopropylamide in THF and subsequent alkylation of the alkoxide with 3-bromoprionamide or 4-bromobutanamide can yield the carboxamido-ethers (29) and (30), respectively.

Synthesis Example 12

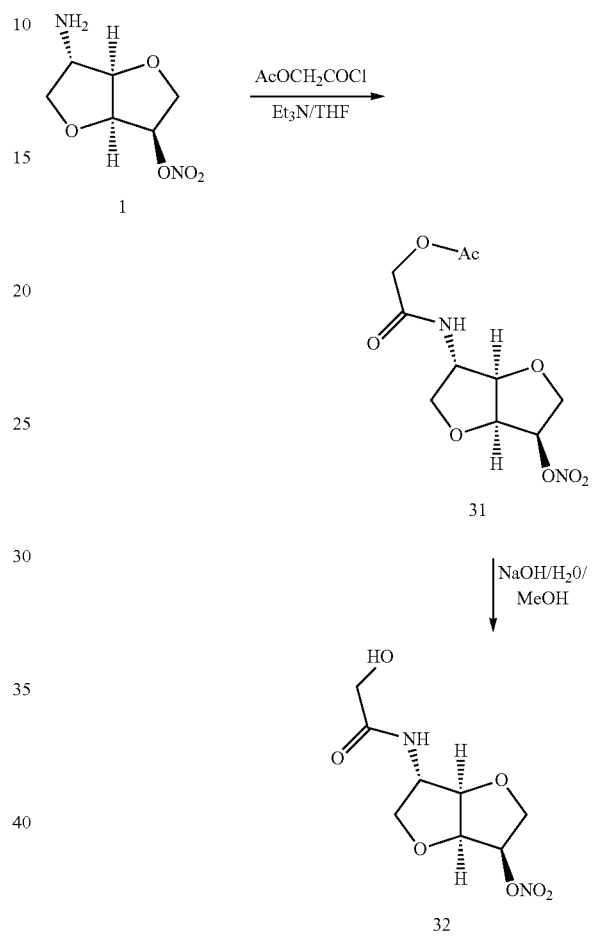

Treatment of 2-amino-isosorbide-5-mononitrate (1) with acetoxyacetyl chloride in the presence of triethylamine in THF can produce the amide adduct (31). Hydrolysis of the acetate with sodium hydroxide solution can produce the hydroxyl amide (32).

Synthesis Example 13

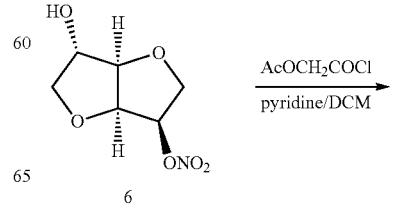

-continued

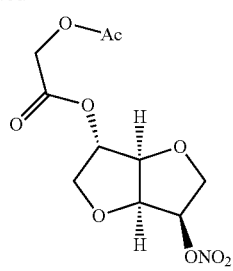

33

Bu₂SnO ↓

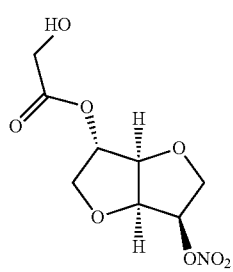

34

Treatment of isosorbide-5-mononitrate (6) with acetoxy-acetyl chloride in the presence of triethylamine in THF can produce the ester adduct (33). Hydrolysis of the acetate with dibutyl tin oxide will produce the glycolic acid adduct (34).

Synthesis Example 14

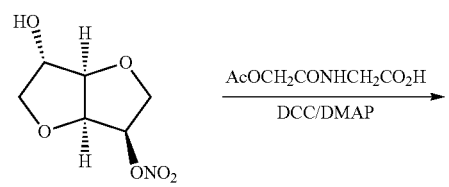

1

AcOCH₂CONHCH₂CO₂H / DCC →

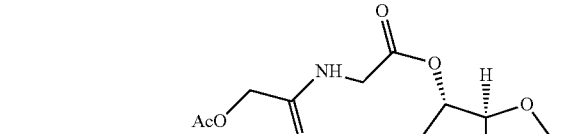

35

NaOH/BuN + HSO₄
THF or Me₃Sn₄OH ↓

-continued

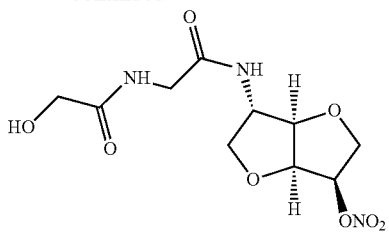

36

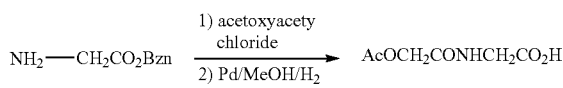

$NH_2-CH_2CO_2Bzn \xrightarrow[\text{2) Pd/MeOH/H}_2]{\text{1) acetoxyacety chloride}} AcOCH_2CONHCH_2CO_2H$ The N-acetoxyacetylglycine can be prepared by treatment of benzyl glycine with acetoxyacetyl chloride in the presence of triethylamine, followed by hydrogenolysis of the benzyl ester in the presence of palladium catalyst. Treatment of 2-amino-isosorbide-5-mononitrate (1) with acetoxy acetyl glycine in DCM in the presence of DCC can produce the acetylated amide adduct (35). Removal of the acetate can be accomplished by reaction with KOH in methanol solution or with trimethyl tin hydroxide.

Synthesis Example 15

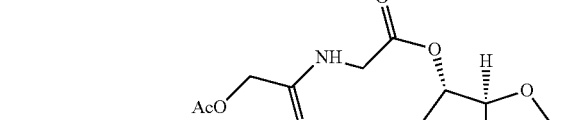

6

AcOCH₂CONHCH₂CO₂H / DCC/DMAP →

37

Me₃SnOH, 1,2 dichoroethane ↓

38

Treatment of isosorbide-5-mononitrate (6) with acetoxy acetyl glycine in DCM in the presence of DCC/DMP can produce the acetylated ester adduct (37). Removal of the acetate can be accomplished by reaction with trimethyl tin hydroxide.

Synthesis Example 16

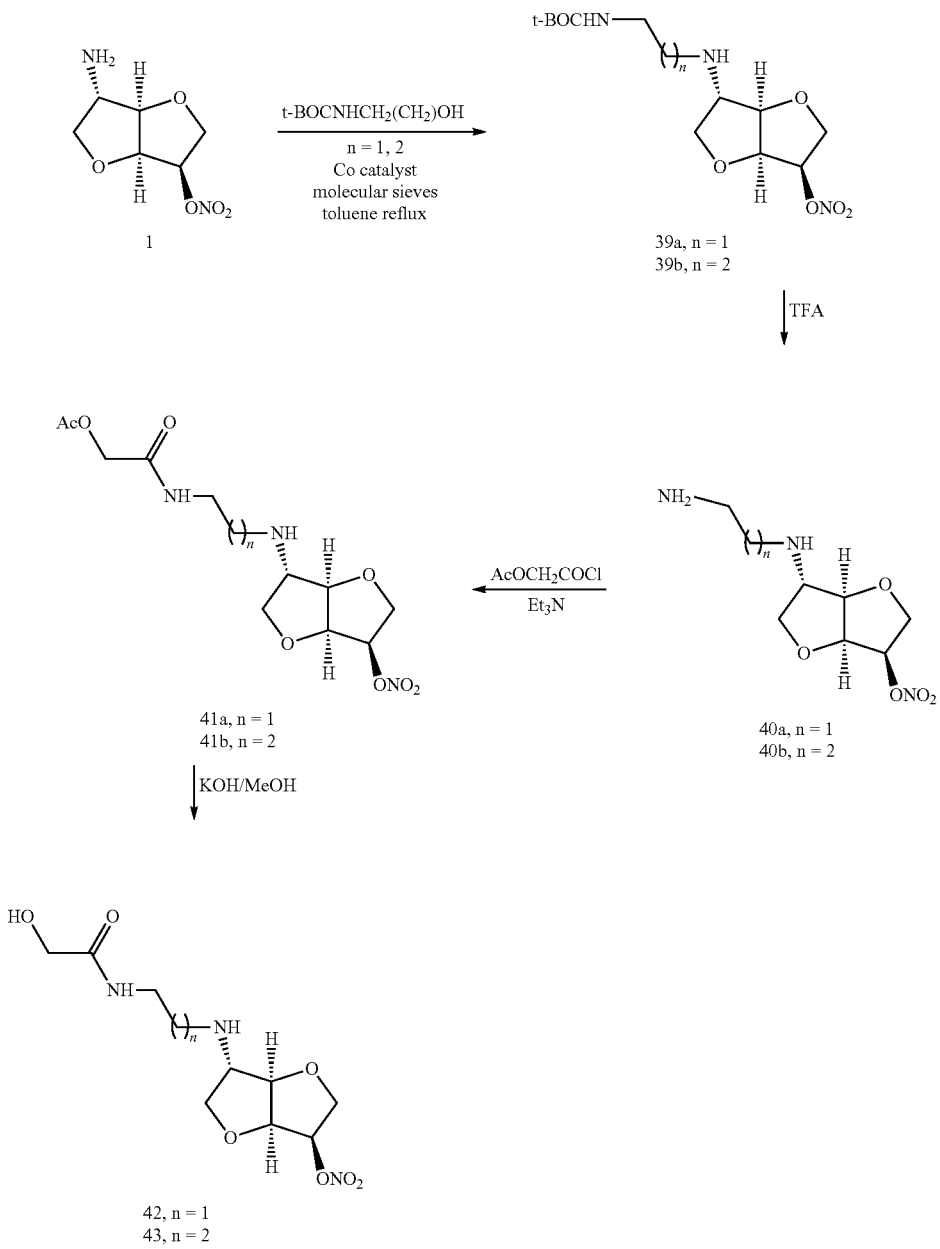

Treatment of 2-amino-isosorbide-5-mononitrate (1) with N-t-BOC-aminoethanol or N-t-BOC-3-aminopropanol in the presence of cobalt catalyst and molecular sieves in toluene at elevated temperatures can provide the protected amino compounds (39). Removal of the protecting group can be accomplished using TFA, which can give the unprotected primary amines (40). Reaction of the amines (40) with acetoxyacetyl chloride in the presence of trimethylamine can provide the amides (41), and subsequent treatment with KOH in methanol can afford the hydroxyacetamides (42 and 43).

Synthesis Example 17

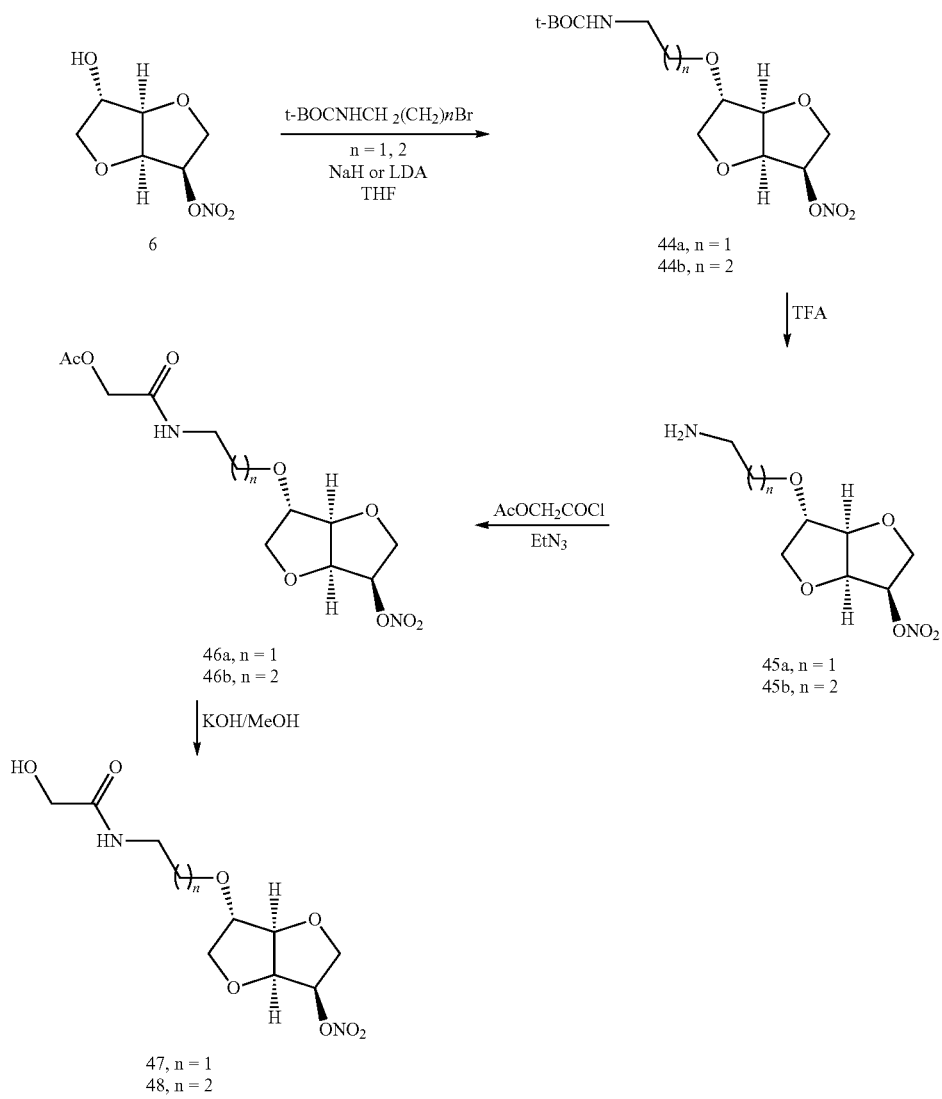

Deprotonation of isosorbide-5-mononitrate (6) with sodium hydride or LDA in THF followed by the addition of N-t-BOC-aminoethyl bromide or N-t-BOC-3-aminopropyl bromide can give the protected ethers (44). Deprotection of the amino groups using TFA can give the primary amines (45), which upon treatment with acteoxyacetyl chloride can give the amides (46). Hydrolysis of the acetate using KOH in MeOH can afford the hydroxacetamides (47 and 48).

Biology

There are two main indications for the present compounds. The first indication is as an antianginal agent. The compounds are expected to improve exercise capacity in the setting of coronary artery disease with the drugs acting as coronary vasodilators. The second indication is for secondary prevention of cardiovascular diseases and in this application vasodilatation is sought as well as ischemic preconditioning.

The experiments described herein are used to test if the present compounds are useful for at least the two main indications. The experiments are to determine the effects of the present compounds and hypoxia on generation of ROS (reactive oxygen species) and markers of inflammation and ischemic preconditioning as well as mediators of vascular smooth muscle relaxation using human aortic endothelial cells (HAECs) and peripheral blood mononuclear cells (PBMC) ex vivo. Primary HAECs, isolated from normal, healthy human adults, can be purchased from Thermo Fisher Scientific (Grand Island, N.Y.) and cultured in Medium 200. Peripheral blood mononuclear cells can be used as part of the determination of the effects of the present compounds ex vivo as referenced below.

Cell cultures can be maintained in a Biospherix (Lacona, N.Y.) humidified cell culture incubator with dynamic control of oxygen and carbon dioxide in an enclosed environment encompassing all aspects of cell manipulation. The medium can be prepared with a pH of 7.3. Incubator conditions can be either normoxic (21% $O_2$, 5% $CO_2$) or hypoxic (1% $O_2$, 5% $CO_2$, balance $N_2$) in a humidified incubator with an interior temperature of 37° C. (using a controlled incubator with $CO_2/O_2$ monitoring and $CO_2/N_2$ gas sources). The medium will be equilibrated to the environmental gas conditions overnight before cellular exposure. As early as possible, and in some cases in primary culture, cells will be incubated with experimental gas mixtures for varied periods. Reoxygenation can be prevented using an enclosed environmental chamber with gloved cell access. Periodic analysis of the cell culture medium with pH, $pCO_2$, and $pO_2$ electrodes can assure a controlled environment.

HAECs can be exposed to either the normoxic condition (20% oxygen) or the hypoxic condition (1% oxygen) for 1 h (for ROS measurement,) 2 h (for determination of transcription factor activity,) 4 h (for determination of inflammatory mediator genes) or 16 h (for determination of inflammatory mediator proteins) both with and without the presence of a compound of the present invention. Dihydroethidium (DHE) and 2',7'-dichloro-fluorescein (DCF) fluorescence assays can be conducted to measure intracellular levels of ROS such as superoxide anion and hydrogen peroxide. DNA-binding activities of pro-inflammatory transcription factors (NF-κB and AP-1) in HAECs can be analyzed by electrophoretic mobility shift assay (EMSA). The mRNA and protein expression levels of the inflammatory mediator IL-1β can be measured in HAECs cultured in normoxia vs. hypoxia in the setting of lipopolysaccharide (LPS) stimulation as previously demonstrated. (Folco, Sukhova, Quillard, & Libby, 2014) Other markers (TNF-α, IL-4, IL-6, IL-10, IL-12, IL-13, IFN-γ, UT-B, eNOS, COX-2 and MCP-1) can be examined in stimulated HAECs. The mRNA and protein expression levels can be measured by quantitative real-time reverse transcriptase-polymerase chain reaction (RT-PCR) and enzyme-linked immunosorbent assay (ELISA). ELISA can be used for analysis of select mediators of relevant endothelial responses, such as $PGE_2$, after stimulation of HAECs in primary culture. Metabolism can be comprehensively assessed using established protocols through a combination of high resolution respirometry and Seahorse extracellular flux analysis to indicate the contributions of mitochondria vs. glycolysis in patient cells.

Activation levels of relevant transcription factors can be determined by measuring DNA-binding activities of nuclear extracts isolated from HAECs in an EMSA. HAECs can be treated as indicated above and the cells incubated with lysis buffer (10 mM Tris-HCl, pH 8.0, 60 mM KCl, 1 mM ethylenediaminetetraacetic acid (EDTA), 1 mM dithiothreitol, 100 μM phenyl-methylsulfonyl fluoride, 0.1% NP-40), lysed for 5 min on ice, and centrifuged at 600×g for 4 min at 4° C. to collect nuclei. Then, the nuclear pellets can be washed with lysis buffer without NP-40, lysed in nuclear extract buffer (20 mM Tris-HCl, pH 8.0, 420 mM NaCl, 1.5 mM $MgCl_2$, 0.2 mM EDTA, 25% glycerol) for 10 min on ice, and centrifuged at 18,300×g for 15 min at 4° C. Supernatants, which contain nuclear extracts, can be frozen immediately on dry ice and transferred to −80° C. until analysis. Binding reactions can be performed with 4 μg of nuclear protein extracts, 10 mM Tris-Cl, pH 7.5, 50 mM NaCl, 1 mM EDTA, 0.1 mM dithiothreitol, 10% glycerol, and 2 μg of poly[dI-dC]. After adding the reagents, the mixture can be incubated for 25 min at room temperature. Then, biotin-labeled specific oligonucleotide probe can be added and/or unlabeled controls, and the binding mixture can be incubated for 25 min at room temperature. Competition studies can be performed by the addition of a molar excess of unlabeled oligonucleotide to the binding reaction. Resultant protein-DNA complexes can be electrophoresed on a non-denaturing 5% polyacrylamide gel using 0.25× TBE buffer (50 mM Tris-Cl, 45 mM boric acid, 0.5 mM EDTA, pH 8.4) for 3 h at 150 V. This is a variation on the LightShift Chemiluminescent EMSA kit (ThermoScientific, Rockford, Ill.).

Quantitative real-time polymerase chain reaction (QRT-PCR) assays can be employed. Fluorogenic 5'-nuclease assay technology with probes and primers (Applied Biosystems, Foster City, Calif.) can be used for gene expression analyses. HAECs can be treated as indicated above and total RNA can be isolated from HAECs using RNeasy Mini Kit (Qiagen, Valencia, Calif.). 1 μg of total RNA can be reverse transcribed at 25° C. for 15 min, 42° C. for 45 min, and 99° C. for 5 min in 20 μL of 5 mM $MgCl_2$, 10 mM Tris-HCl, pH 9.0, 50 mM KCl, 0.1% Triton X-100, 1 mM dNTP, 1 unit/μL of recombinant RNasin, 15 unit/μg of Avian Myeloblastosis Virus (AMV) reverse transcriptase, and 0.5 μg of random hexamers. Amplification of individual genes can be performed on the Applied Biosystems 7300 Real-Time PCR System using Universal PCR Master Mix and a standard thermal cycler protocol (50° C. for 2 min before the first cycle, 95° C. for 15 sec and 60° C. for 1 min, repeated 45 times). Gene expression assay reagents for human TNF-α, IL-4, IL-6, IL-10, IL-12, IL-13, IFN-γ, UT-B, COX-2, eNOS, MCP-1, and glyceraldehyde-3-phosphate dehydrogenase (GAPDH) can be used for specific probes and primers of PCR amplifications. The threshold cycle (CT), which indicates the fractional cycle number at which the amount of amplified target gene reaches a fixed threshold, can be determined from each well using the Applied Biosystems Sequence Detection Software.

The intracellular levels of ROS can be measured by DHE and DCF fluorescence staining using a fluorescence microscope. HAECs can be treated as indicated above and the cells loaded with either DHE or carboxy-$H_2$DCF-DA (Invitrogen Corp., Carlsbad, Calif.) at concentration of 5 μM in PBS for 30 min at 37° C. in 5% $CO_2$/95% air, humidified cell culture incubator. HAECs can be washed with PBS and examined on a fluorescence microscope. The DHE or DCF fluorescence intensity of acquired digital images can be quantified accordingly.

The effects of the present compounds on hypoxia-mediated release of NO from endothelial cells can be measured by isolating cells with membrane-permeable 4,5-Diaminofluorescein diacetate (DAF-2 diacetate), which leads to accumulation of membrane impermeable intracellular DAF-2. DAF-2 reacts with NO to form the highly fluorescent triazolofluoresciein (DAF-2T) and this can be detected by spectrofluorimetry of supernatants. (Leikert et al., 2001)

Parallel studies can be used to test the effect of the present compounds on cellular ROS homeostasis and metabolism in cellular metabolic assays. Plated cells from different experimental groups can be studied on a Seahorse extracellular flux analyzer. Oxygen consumption rates (mitochondrial function) and extracellular acidification rates (glycolysis) can be measured under basal conditions, maximally respiring conditions, and after inhibiting mitochondrial bioenergetics using established methods. (Dai et al., 2016) Parallel subsets of cells can be placed in Oroboros High Resolution respirometer chambers for the simultaneous measurement of cellular ROS and metabolism using established protocols. (Alleman et al., 2016)

Peripheral blood mononuclear cells and serum can be obtained from human volunteers. Patients can be used as their own controls in a clinical trial designed to test the effects of the present compounds on patients with ischemic cardiomyopathy (including a history of myocardial infarction) and indications for secondary prevention. The study can be limited to 5×8 mL tubes of blood per draw, from which it can be expected to derive 2 mL of plasma-derived serum and 8×10⁶ PBMCs per tube using the BD Vacutainer CPT with sodium heparin (Franklin Lakes, N.J.) This contains sodium heparin anticoagulant with a FICOLL Hypaque density fluid and a polyester gel barrier that separates the two liquids. The tube can be centrifuged at room temperature for 15 minutes at 1500 g. Plasma can be obtained as the supernatant above a layer of mononuclear cells and platelets on top of the density solution. Serum can be derived from the plasma supernatant by adding $CaCl_2$ to a final concentration of 20 mM and allowing to clot at room temperature for 4 hours, followed by freezing the clotted plasma at −20° C. overnight, thawing, and centrifugation of the serum remaining at 5000 g for at least 5 min. Serum can be filtered, aliquoted and frozen at −20° C. PBMCs can be washed twice in phosphate buffered saline after separation by centrifuge for 10-15 minutes at 18-20° C., 400 g and then resuspended in AIM V medium (Life Technologies) at 8×106 cells/2 mL and then divided into aliquots of 1×106 cells. Cultures can be maintained in a Biospherix (Lacona, N.Y.) humidified cell culture incubator with dynamic control of oxygen and carbon dioxide in an enclosed environment encompassing all aspects of cell manipulation.

DHE/DCF fluorescence assays, real-time RT-PCR, ELISA, EMSA, and reporter gene assays can be performed to determine ROS generation, mRNA, and protein expression of mediators of ischemic preconditioning, including downstream products of endothelial nitric oxide synthase and cyclooxygenase-2 expression. The products of eNOS and COX-2 can confirm the therapeutic value of the present compounds compared with control. Toxicity can be assessed by the metabolic effects of the present compounds using Seahorse technology.

Tables 1-3 shows the structures of compounds of the present invention that can be synthesized as described above.

TABLE 1

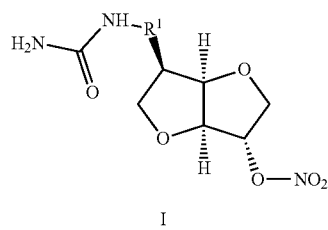

I

| Ex. # | R¹ |
|---|---|
| 1. | Absent |
| 2. | $(CH_2)_2O$ |
| 3. | $(CH_2)_2NH$ |
| 4. | $(CH_2)_3O$ |
| 5. | $(CH_2)_3NH$ |
| 6. | $CH_2C(=O)O$ |
| 7. | $CH_2C(=O)NH$ |

TABLE 2

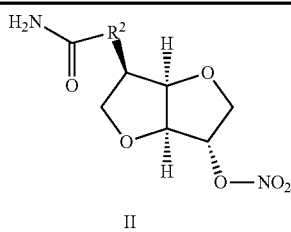

II

| Ex. # | R² |
|---|---|
| 1. | $(CH_2)_2O$ |
| 2. | $(CH_2)_2NH$ |
| 3. | $(CH_2)_3O$ |
| 4. | $(CH_2)_3NH$ |
| 5. | $CH_2C(=O)O$ |
| 6. | $CH_2C(=O)NH$ |
| 7. | $CH_2OC(=O)O$ |
| 8. | $CH_2OC(=O)NH$ |
| 9. | $CH_2NHC(=O)O$ |
| 10. | $CH_2NHC(=O)NH$ |

TABLE 3

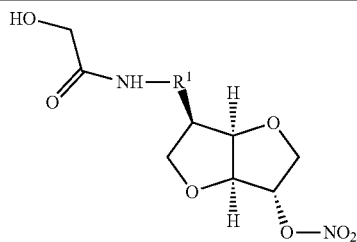

III

| Ex. # | R¹ |
|---|---|
| 1. | Absent |
| 2. | $(CH_2)_2O$ |
| 3. | $(CH_2)_2NH$ |
| 4. | $(CH_2)_3O$ |
| 5. | $(CH_2)_3NH$ |
| 6. | $CH_2C(=O)O$ |
| 7. | $CH_2C(=O)NH$ |

Numerous modifications and variations of the present invention are possible in light of the above teachings. It is therefore to be understood that within the scope of the appended claims, the invention may be practiced otherwise than as specifically described herein.

BIBLIOGRAPHY

Alleman, R. J., Tsang, A. M., Ryan, T. E., Patteson, D. J., McClung, J. M., Spangenburg, E. E. et al. (2016). Exercise-induced protection against reperfusion arrhythmia involves stabilization of mitochondrial energetics. American Journal of Physiology-Heart and Circulatory Physiology, 310, H1360-H1370.

Benjamin, E. J., Muntner, P., Alonso, A., Bittencourt, M. S., Callaway, C. W., Carson, A. P. et al. (2019). Heart Disease and Stroke Statistics-2019 Update: A Report From the American Heart Association. Circulation, 139, e56-e528.

Chou, T. C., Talalay, P. (1984) Quantitative analysis of dose-effect relationships: the combined effects of multiple drugs or enzyme inhibitors. Advances in Enzyme Regulation, 22, 27-55

Dai, W., Cheung, E., Alleman, R. J., Perry, J. B., Allen, M. E., Brown, D. A. et al. (2016). Cardioprotective effects of mitochondria-targeted peptide SBT-20 in two different models of rat ischemia/reperfusion. Cardiovascular Drugs and Therapy, 30, 559-566.

Folco, E. J., Sukhova, G. K., Quillard, T., & Libby, P. (2014). Moderate hypoxia potentiates interleukin-1beta production in activated human macrophages. Circulation Research, 115, 875-883.

Guo, Y., Tukaye, D. N., Wu, W. J., Zhu, X., Book, M., Tan, W. et al. (2012). The COX-2/PGI2 receptor axis plays an obligatory role in mediating the cardioprotection conferred by the late phase of ischemic preconditioning. PLoS One., 7, e41178.

Ji, Y.-S., Xu, Q., & Schmedtje, J. F., Jr. (1998). Hypoxia induces high-mobility-group protein I(Y) and transcription of the cyclooxygenase-2 gene in human vascular endothelium. Circulation Research, 83, 295-304.

Leikert, J. F., Räthel, T. R., Müller, C., Vollmar, A. M., & Dirsch, V. M. (2001). Reliable in vitro measurement of nitric oxide released from endothelial cells using low concentrations of the fluorescent probe 4,5-diaminofluorescein. FEBS Letters, 506, 131-134.

Li, Q., Guo, Y., Tan, W., Ou, Q., Wu, W. J., Sturza, D. et al. (2007). Cardioprotection Afforded by Inducible Nitric Oxide Synthase Gene Therapy Is Mediated by Cyclooxygenase-2 via a Nuclear Factor-KB Dependent Pathway. Circulation, 116, 1577-1584.

Li, X., Chen, G, Yang, B. (2012) Urea transporter physiology studied in knockout mice. Frontiers in Physiology, 3:217.

Sands, J. M. (1999). Regulation of Renal Urea Transporters. Journal of the American Society of Nephrology, 10, 635-646.

Schmedtje, J. F., Jr., Ji, Y.-S., Liu, W.-L., DuBois, R. N., & Runge, M. S. (1997). Hypoxia induces cyclooxygenase-2 via the NF-κB p65 transcription factor in human vascular endothelial cells. Journal of Biological Chemistry, 272, 601-608.

Semenza, G. L. (2019). Pharmacologic Targeting of Hypoxia-Inducible Factors. Annual Review of Pharmacology and Toxicology, 59, 379-403.

Shayakul, C., Clemencon, B., & Hediger, M. A. (2013). The urea transporter family (SLC14): physiological, pathological and structural aspects. Molecular Aspects of Medicine, 34, 313-322.

Sun, Y., Lau, C. W., Jia, Y., Li, Y., Wang, W., Ran, J., Li, F., Huang, Y., Zhou, H., Yang, B. Functional inhibition of urea transporter UT-B enhances endothelial-dependent vasodilatation and lowers blood pressure via L-arginine-endothelial nitric oxide synthase-nitric oxide pathway. Scientific Reports 2016, 6, 18697.

Wagner, L., Klein, J. D., Sands, J. M., & Baylis, C. (2002). Urea transporters are distributed in endothelial cells and mediate inhibition of L-arginine transport. American Journal of Physiology: Renal Physiology, 283, F578-F582.

Wang, X., Wu, L., Aouffen, M., Mateescu, M., Nadeau, R., & Wang, R. (1999). Novel cardiac protective effects of urea: from shark to rat. British Journal of Pharmacology, 128, 1477-1484.

Xiao, S.; Erdely, A.; Wagner, L.; Baylis, C. Uremic levels of BUN do not cause nitric oxide deficiency in rats with normal renal function. American Journal of Physiology-Renal Physiology 2001, 280, F996-F1000.

Xu, Q., Ji, Y. S., & Schmedtje, J. F., Jr. (2000). Sp1 increases expression of cyclooxygenase-2 in hypoxic vascular endothelium—Implications for the mechanisms of aortic aneurysm and heart failure. Journal of Biological Chemistry, 275, 24583-24589.

Zhao, D., Sonawane, N. D., Levin, M. H., & Yang, B. (2007). Comparative transport efficiencies of urea analogues through urea transporter UT-B. Biochimica et Biophysica Acta (BBA)—Biomembranes, 1768, 1815-1821.

What is claimed is:

1. A compound of formula I, II, or III:

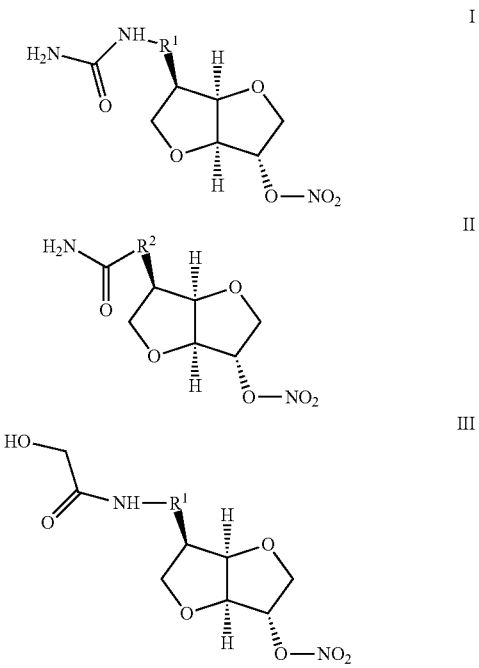

wherein:
R$^1$ is absent;
alternatively, R$^1$ is selected from: (CH$_2$)$_2$O, (CH$_2$)$_2$NH, (CH$_2$)$_3$O, (CH$_2$)$_3$NH, CH$_2$C(=O)O, and CH$_2$C(=O)NH; and,
R$^2$ is selected from: (CH$_2$)$_2$O, (CH$_2$)$_2$NH, (CH$_2$)$_3$O, (CH$_2$)$_3$NH, CH$_2$C(=O)O, CH$_2$C(=O)NH, CH$_2$OC(=O)O, CH$_2$OC(=O)NH, CH$_2$NHC(=O)O, and CH$_2$NHC(=O)NH;
or a pharmaceutically acceptable salt thereof.

2. A compound of claim 1, wherein the compound is of Formula I:

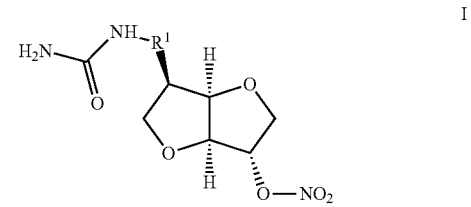

or a pharmaceutically acceptable salt thereof.

3. A compound of claim 2, wherein:
R$^1$ is absent;
or a pharmaceutically acceptable salt thereof.

4. A compound of claim 2, wherein:

R$^1$ is selected from: (CH$_2$)$_2$O, (CH$_2$)$_2$NH, (CH$_2$)$_3$O, and (CH$_2$)$_3$NH;

or a pharmaceutically acceptable salt thereof.

5. A compound of claim 2, wherein:

R$^1$ is (CH$_2$)$_2$O or a pharmaceutically acceptable salt thereof.

6. A compound of claim 2, wherein:

R$^1$ is (CH$_2$)$_2$NH or a pharmaceutically acceptable salt thereof.

7. A compound of claim 2, wherein:

R$^1$ is CH$_2$C(=O)O or a pharmaceutically acceptable salt thereof.

8. A compound of claim 2, wherein:

R$^1$ is CH$_2$C(=O)NH or a pharmaceutically acceptable salt thereof.

9. A compound of claim 1, wherein the compound is of Formula II:

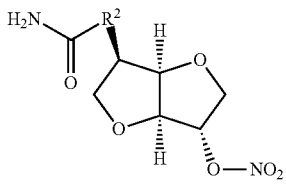

II or a pharmaceutically acceptable salt thereof.

10. A compound of claim 9, wherein:

R$^2$ is selected from: (CH$_2$)$_2$O, (CH$_2$)$_2$NH, (CH$_2$)$_3$O, (CH$_2$)$_3$NH, CH$_2$OC(=O)O, CH$_2$OC(=O)NH, CH$_2$NHC(=O)O, and CH$_2$NHC(=O)NH;

or a pharmaceutically acceptable salt thereof.

11. A compound of claim 9, wherein:

R$^2$ is CH$_2$C(=O)O or a pharmaceutically acceptable salt thereof.

12. A compound of claim 9, wherein:

R$^2$ is CH$_2$C(=O)NH or a pharmaceutically acceptable salt thereof.

13. A compound of claim 1, wherein the compound is of Formula I:

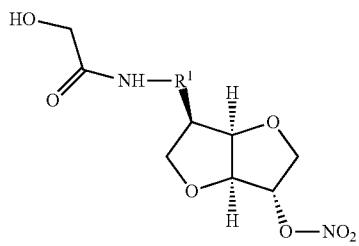

III or a pharmaceutically acceptable salt thereof.

14. A compound of claim 13, wherein:

R$^1$ is absent;

or a pharmaceutically acceptable salt thereof.

15. A compound of claim 13, wherein:

R$^1$ is selected from: (CH$_2$)$_2$O, (CH$_2$)$_2$NH, (CH$_2$)$_3$O, and (CH$_2$)$_3$NH;

or a pharmaceutically acceptable salt thereof.

16. A compound of claim 13, wherein:

R$^1$ is CH$_2$C(=O)O or a pharmaceutically acceptable salt thereof.

17. A compound of claim 13, wherein:

R$^1$ is CH$_2$C(=O)NH or a pharmaceutically acceptable salt thereof.

18. A pharmaceutical composition, comprising: a therapeutically effective amount of a compound of claim 1 and a pharmaceutically acceptable carrier.

19. A method of treating a disease, comprising: administering to a mammal in need thereof a therapeutically effective amount of a compound of claim 1, wherein the disease is a cardiovascular disease.

20. The method of treating a disease of claim 19, wherein the cardiovascular disease is selected from: coronary artery disease, myocardial infarction, heart failure, cardiac arrhythmia, electrophysiological disorders of the heart, congenital cardiovascular anomalies, developmental cardiovascular anomalies, inflammatory cardiomyopathy, Kawasaki disease, infectious cardiomyopathy, sudden death/cardiac arrest, atherosclerosis, atherosclerotic cardiovascular diseases, cardiac valve disease, venous insufficiency, cardiac thrombosis, vascular thrombosis, thromboembolism, peripheral arterial disease, aortic aneurysm, aortic dissection, vascular aneurysm, vascular dissection, stroke, systemic hypertension, and pulmonary hypertension.

\* \* \* \* \*